(12) United States Patent
Tsujii et al.

(10) Patent No.: US 7,945,015 B2
(45) Date of Patent: May 17, 2011

(54) X-RAY IMAGING APPARATUS AND CONTROL METHOD THEREOF

(75) Inventors: Osamu Tsujii, Kawasaki (JP); Keiji Tsuchiya, Kawasaki (JP); Masahiko Okunuki, Akiruno (JP)

(73) Assignee: Canon Kabushiki Kaisha, Tokyo (JP)

( * ) Notice: Subject to any disclaimer, the term of this patent is extended or adjusted under 35 U.S.C. 154(b) by 253 days.

(21) Appl. No.: 12/395,773

(22) Filed: Mar. 2, 2009

(65) Prior Publication Data
US 2009/0232272 A1   Sep. 17, 2009

(30) Foreign Application Priority Data
Mar. 17, 2008   (JP) .................................. 2008-068355

(51) Int. Cl.
*G01N 23/00* (2006.01)
(52) U.S. Cl. ............... 378/26; 378/21; 378/62; 378/124; 378/149
(58) Field of Classification Search .................... 378/21, 378/25, 26, 62, 92, 119, 121, 122, 124–126, 378/147, 149, 197
See application file for complete search history.

(56) References Cited

U.S. PATENT DOCUMENTS

| 2007/0280408 A1* | 12/2007 | Zhang ............................. 378/10 |
| 2009/0232270 A1 | 9/2009 | Okunuki et al. .............. 378/124 |
| 2009/0316860 A1 | 12/2009 | Okunuki et al. .............. 378/122 |

FOREIGN PATENT DOCUMENTS

| JP | 2000-060835 | 2/2000 |
| JP | 2004-089445 | 3/2004 |

* cited by examiner

*Primary Examiner* — Jurie Yun
(74) *Attorney, Agent, or Firm* — Fitzpatrick, Cella, Harper & Scinto

(57) ABSTRACT

An X-ray imaging apparatus includes a multi X-ray generating unit in which multiple X-ray foci are disposed in two-dimensional form at a predetermined pitch in a first direction, and a slit unit having multiple slit members each disposed opposite to its respective X-ray focus. Each slit member has multiple slits arranged in the first direction, and each of the slits forms a slice-formed X-ray beam whose lengthwise direction is a second direction that is different from the first direction. The two-dimensional detection unit detects the X-ray intensity of the formed X-ray beams at the detection surface. The X-ray imaging apparatus executes X-ray imaging at multiple positions while moving the multi X-ray generating unit and the slit unit in the first direction by the amount of the predetermined pitch, while keeping the relative positional relationship therebetween, and reconstructs an X-ray image based on the obtained X-ray intensity.

8 Claims, 13 Drawing Sheets

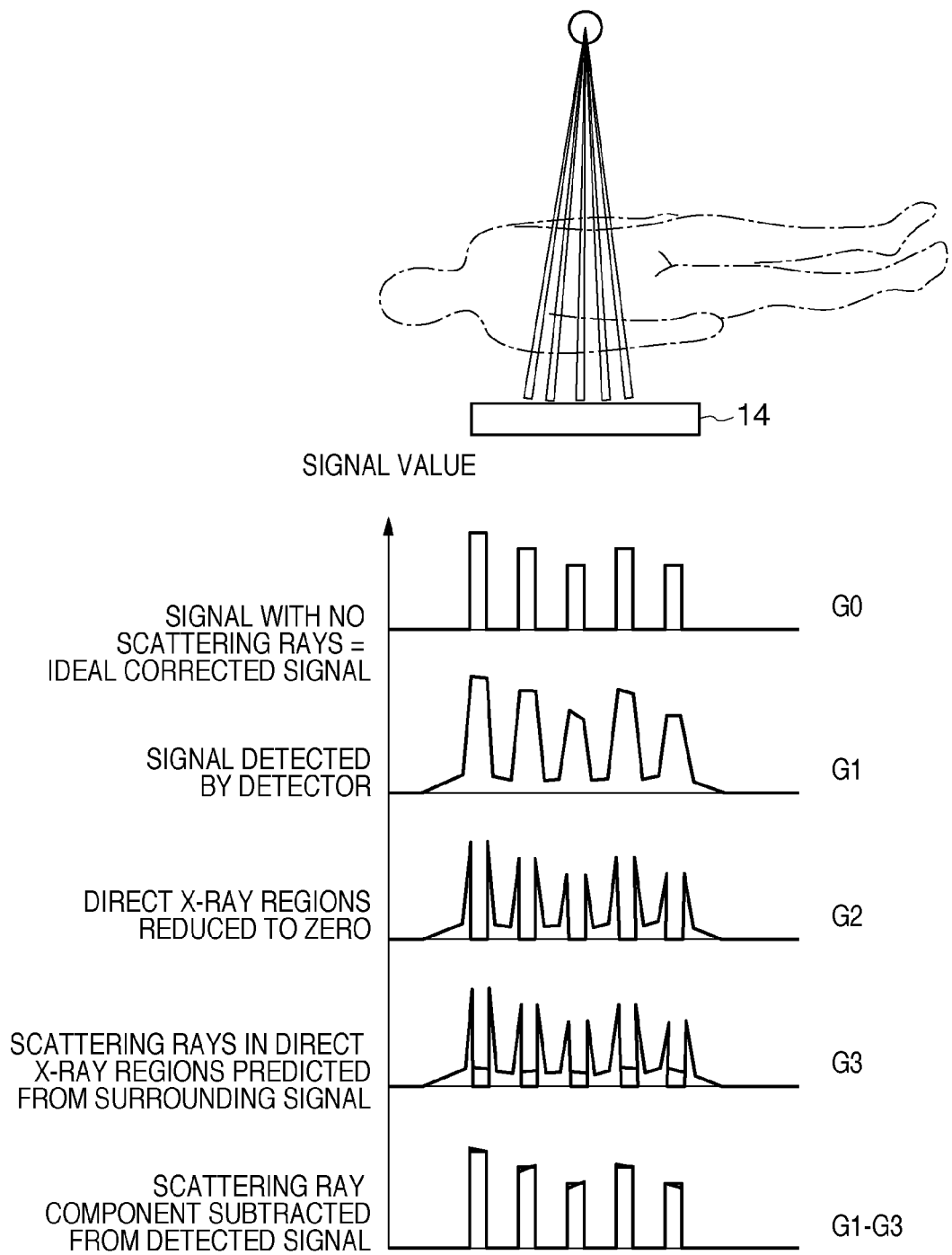

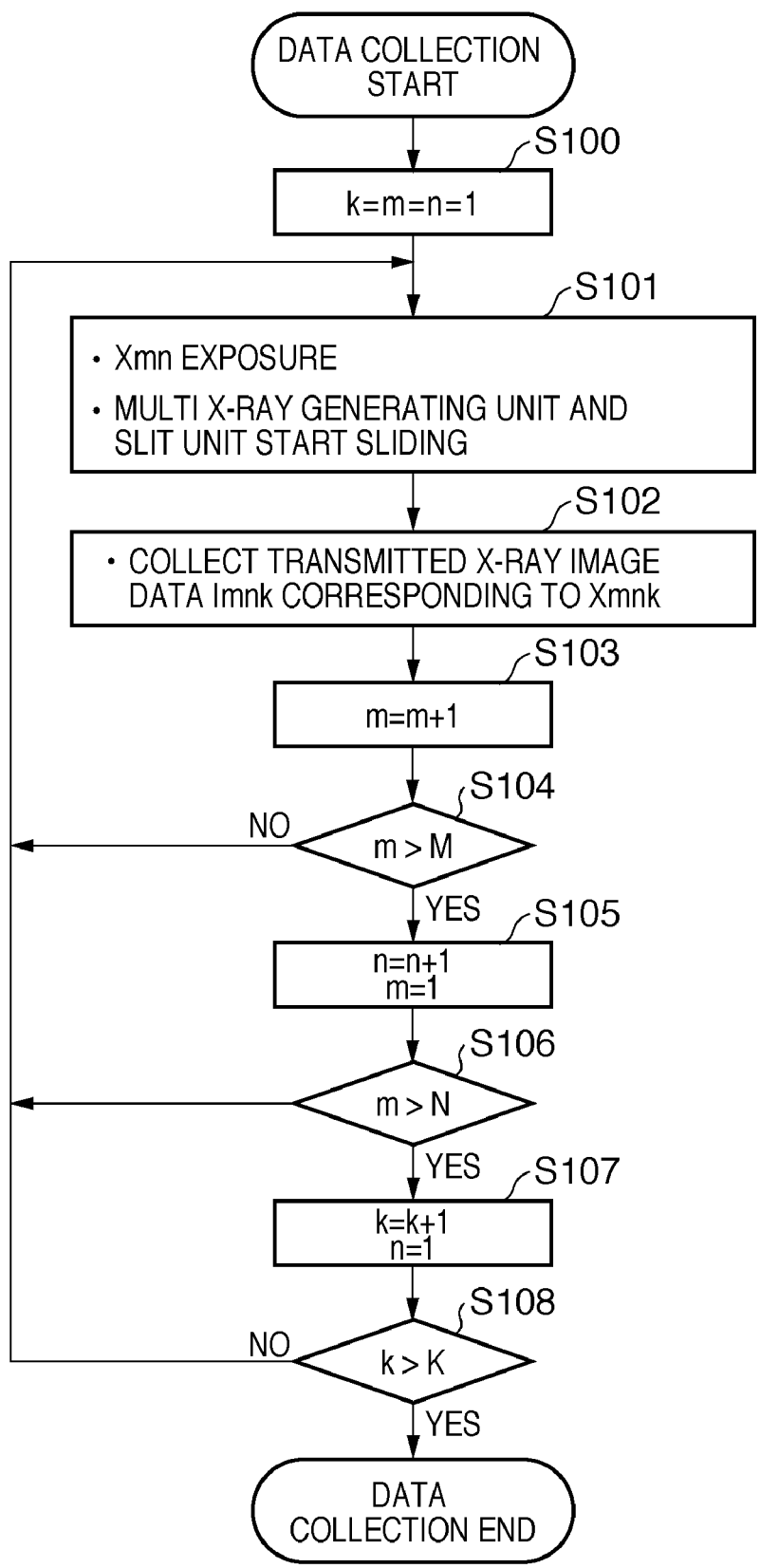

X-RAY IMAGING APPARATUS AND CONTROL METHOD THEREOF

BACKGROUND OF THE INVENTION

1. Field of the Invention

The present invention relates to an X-ray imaging apparatus that uses a multiple X-ray source, and in particular to an apparatus that provides an X-ray tomographic image.

2. Description of the Related Art

A multiple X-ray source that uses carbon nanotubes as cold cathodes is known. This publicly-known X-ray emission apparatus forms a two-dimensional X-ray source by using multiple X-ray tubes utilizing carbon nanotubes as cathodes that emit electrons and disposing X-ray radiation windows, for collecting the X-rays from the X-ray tube, in a two-dimensional arrangement. The X-rays emitted from the two-dimensional X-ray source of the X-ray emission apparatus pass through a subject and are irradiated upon an X-ray image detector. The X-ray image detector generates an image signal of the X-ray image based on the intensity of the irradiated X-rays. A collimater, in which capillaries are arranged two-dimensionally in a sieve-like form, is disposed between the two-dimensional X-ray source of the X-ray emission apparatus and the subject, so that the axial direction of the capillaries follows the same direction as the direction between the two-dimensional X-ray source and the subject (see Japanese Patent Laid-Open No. 2004-089445 (called "Patent Document 1" hereinafter)).

Meanwhile, a technique whereby a tomographic image of a subject is calculated based on transmitted X-ray images created using multiple X-ray sources is known. In this publicly-known technique, a radiation source that irradiates a target surface with an electron beam, causing the emission of X-rays, and forms the X-rays into beam form by passing them through a collimater hole, is used. Many collimater holes are provided on the surface. The X-rays that pass through the subject are sequentially detected by a radiation detector, while scanning the electron beam and sequentially switching the collimater hole. A transmitted image forming means obtains transmitted image information based on the detection signals from the radiation detector that hold subject image information for each pixel point. Because the X-rays enter into the radiation detector directly from the collimater holes, and almost no scattering rays enter, no scattering ray information is included in the transmitted image information; thus, three-dimensional image information that includes no scattering ray information can be obtained (see Japanese Patent Laid-Open No. 2000-060835 (hereinafter called "Patent Document 2")).

The X-ray imaging system disclosed in Patent Document 2 is formed in a quadrangular cone shape, as viewed in the direction extending from the focal point to the detector. The detection target is therefore captured over a wide range in regions close to the detector, and over a narrow range in regions far from the detector. When this phenomenon is observed in the vicinity of the X-ray sources, projection data of the detection target cannot be acquired in the pitch interval between multiple X-ray sources. In other words, data missing regions arise in the pitch areas between X-ray sources. This problem becomes more marked the larger the enlargement rate of the imaging system is.

Another problem is the reciprocal relationship between scattering ray removal and X-ray usage efficiency. In conventional X-ray imaging, the cone angles of the quadrangular cone-shape formed by the X-ray beam are enlarged, increasing the X-ray usage efficiency, and a large subject region is captured at one time. However, when a large region is irradiated with X-rays at one time, the resolution of the image decreases due to scattering rays. Although a scattering ray suppression grid can be used to suppress such scattering rays, the scattering ray suppression grid is disadvantageous because it dampens valid straight rays as well. Patent Document 2 therefore reduces the cone angles, which reduces the scattering rays, but reducing the cone angles also causes a drop in the X-ray usage efficiency.

SUMMARY OF THE INVENTION

It is an aspect of the present invention to reduce or eliminate data missing regions arising in pitch areas between X-ray sources, and to reduce the influence of scattering rays, in X-ray imaging that uses a multiple X-ray source.

According to one aspect of the present invention, there is provided an X-ray imaging apparatus comprising: a multi X-ray generating unit in which multiple X-ray foci are disposed in two-dimensional form at a predetermined pitch in a first direction; a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction; a two-dimensional detection unit that detects the X-ray intensity of the X-ray beams formed by the slit unit at the detection surface; a moving unit that moves the multi X-ray generating unit and the slit unit in the first direction while keeping the relative positional relationship therebetween; an executing unit that executes X-ray imaging at multiple positions while the moving unit moves the multi X-ray generating unit and the slit unit by the amount of the predetermined pitch; and a reconstructing unit that reconstructs an X-ray image based on the X-ray intensity obtained through the X-ray imaging executed by the executing unit.

According to another aspect of the present invention, there is provided an X-ray imaging apparatus comprising: a multi X-ray generating unit in which multiple X-ray foci are disposed in two-dimensional form at a predetermined pitch in a first direction; a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction; a two-dimensional detection unit that detects the X-ray intensity of the X-ray beams formed by the slit unit at the detection surface; a moving unit that moves the multi X-ray generating unit and the slit unit in the first direction while changing the relative positional relationship therebetween; an executing unit that executes X-ray imaging at multiple positions while the moving unit moves the multi X-ray generating unit and the slit unit by the amount of the predetermined pitch; and a reconstructing unit that reconstructs an X-ray image based on the X-ray intensity obtained through the X-ray imaging executed by the executing unit.

Furthermore, according to another aspect of the present invention, there is provided a control method for an X-ray imaging apparatus, the apparatus including: a multi X-ray generating unit in which multiple X-ray foci are disposed in two-dimensional form at a predetermined pitch in a first direction; a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction; and a two-dimensional detection unit that detects the X-ray intensity of the X-ray beams formed by the slit unit at the detection surface, the method comprising the steps of: moving the multi X-ray generating unit and the slit unit in the first direction while keeping the relative positional relationship therebetween; executing X-ray imaging at multiple positions while the step of moving moves the multi X-ray generating unit and the slit unit by the amount of the predetermined pitch; and reconstructing an X-ray image based on the X-ray intensity obtained through the X-ray imaging executed in the step of executing.

Furthermore, according to another aspect of the present invention, there is provided a control method for an X-ray imaging apparatus, the apparatus including: a multi X-ray generating unit in which multiple X-ray foci are disposed in two-dimensional form at a predetermined pitch in a first direction; a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction; and a two-dimensional detection unit that detects the X-ray intensity of the X-ray beams formed by the slit unit at the detection surface, the method comprising the steps of: moving the multi X-ray generating unit and the slit unit in the first direction while changing the relative positional relationship therebetween; executing X-ray imaging at multiple positions while the step of moving moves the multi X-ray generating unit and the slit unit by the amount of the predetermined pitch; and reconstructing an X-ray image based on the X-ray intensity obtained through the X-ray imaging executed in the step of executing.

Further features of the present invention will become apparent from the following description of exemplary embodiments with reference to the attached drawings.

BRIEF DESCRIPTION OF THE DRAWINGS

FIG. 6 is a conceptual diagram illustrating scattering ray correction according to the first embodiment.

FIG. 9A is a flowchart illustrating a data collection process according to the first embodiment.

DESCRIPTION OF THE EMBODIMENTS

Exemplary embodiments of the present invention will now be described in detail in accordance with the accompanying drawings.

First Embodiment

Figure 1:
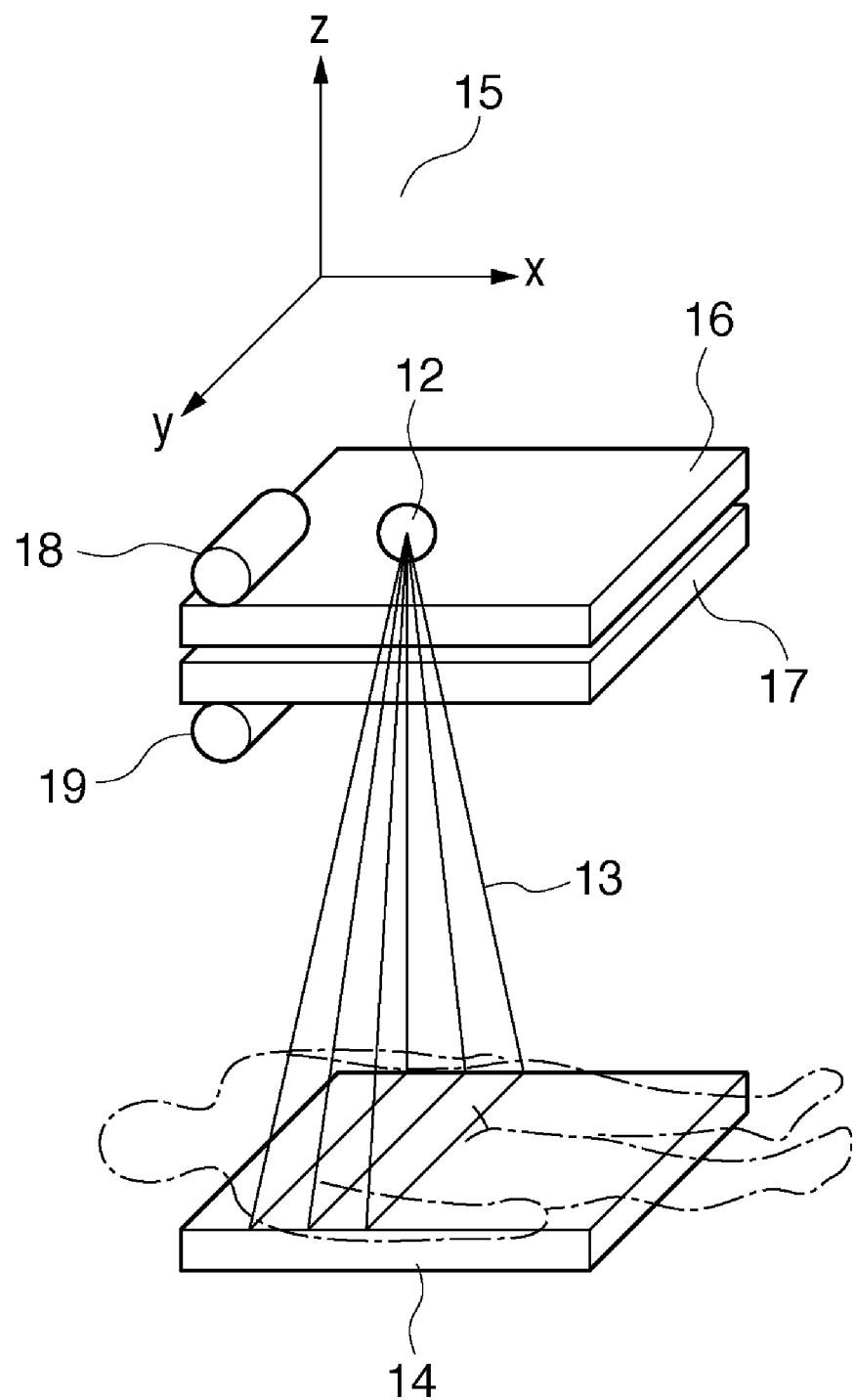
FIG. 1 is a diagram illustrating an imaging system in an X-ray imaging apparatus according to a first embodiment.

FIG. 1 is a diagram illustrating an example of the configuration of an X-ray imaging system according to a first embodiment. A multi X-ray generating unit 16 includes multiple X-ray sources 12, serving as X-ray foci, that emit X-ray beams 13, and collimaters 20 that form the X-ray beams 13 from the X-ray sources 12 primarily (see FIG. 2). Each X-ray source 12 is structured so as to generate X-rays by accelerating electrons from a cold cathode such as carbon nanotubes and causing them to collide with a target. The X-ray sources 12 are arranged two-dimensionally inside the multi X-ray generating unit 16 in, for example, a grid form that has 26 rows, 26 columns, and a grid pitch of 15 mm, resulting in 676 sources. Note, however, that the X-ray sources 12 are not limited to sources that utilize cold cathodes, and may instead utilize thermoelectron sources.

Each X-ray beam 13 is formed secondarily by a slit unit 17. The slit unit 17 is an assemblage of slit boards 21, serving as slit members, provided for each of the X-ray sources 12 (this shall be described later with reference to FIG. 4). A slit board 21 is allocated to each individual X-ray source 12. To be more specific, the slit boards 21 are fabricated and disposed so that the X-ray beams 13 that do not reach the detection surface of a two-dimensional detection unit 14 do not pass through the slit boards 21. This is to prevent X-ray beams 13 that do not contribute to the imaging of a subject from being output.

The cone-shaped X-ray beams 13 that enter into the slit boards 21 are transformed into multiple slice beams by multiple slits provided in the slit boards 21. Note, however, that the formation of the X-ray beams by the slit unit 17 is not limited to such formation of slice beams; the X-ray beams may be formed into grid form as well. When the X-ray beams 13 are to be formed into slice form, the X-ray percolation openings in the slit boards 21 are configured of grooves (slits), whereas when the X-ray beams 13 are to be formed in grid form, the X-ray percolation openings in the slit boards 21 are configured of rows of small holes. Note that even when the X-ray beams are to be formed in grid form, a slice-formed X-ray beam is formed due to multiple X-ray beams passing through multiple X-ray percolation openings. Therefore, in the present specification, X-ray beams obtained after passing through such rows of small holes also fall under the category of slice-formed X-ray beams. In this manner, the slit unit 17 includes multiple slit boards 21, each disposed opposite to its respective X-ray focus, and each of the multiple slit boards 21 includes multiple slits arranged in the X direction, or a first direction. Each of these multiple slits forms X-rays from opposing X-ray foci into a slice-formed X-ray beam whose longitudinal direction is the Y direction, or a second direction, which is different from the abovementioned first direction.

The two-dimensional detection unit 14 detects the X-ray intensity of the X-ray beams formed by the slit means at the detection surface.

The purpose of the slit unit 17 is to reduce scattering rays. When the entire surface of the two-dimensional detection unit is simultaneously irradiated with the X-ray beams 13, an unpredictable amount of scattering rays will occur within the detection surface of the two-dimensional detection unit 14. Conventional techniques therefore dispose a scattering ray removing grid between the subject and the two-dimensional detection unit 14. This scattering ray removing grid is normally fabricated so as to include an imaging focus, and the imaging system is adjusted so that the focus of the X-ray beam and the imaging focus of the scattering ray removing grid match. However, in an imaging system such as that described in the present embodiment, where multiple X-ray beam foci exist, such a scattering ray removing grid cannot be used.

Meanwhile, the lead slits of which the scattering ray removing grid is configured also have an adverse effect of dampening valid X-ray beams 13 as well. In the present embodiment, however, scattering rays are reduced through calculations. To be more specific, the X-ray beams 13 are formed in slice form or grid form, and a region into which X-rays do not enter is set in the two-dimensional detection unit 14. However, in reality, scattering rays enter into even this region into which X-rays do not enter. It is thus possible for this region to detect only the scattering ray signals. The distribution of scattering rays across the entirety of the two-dimensional detection unit 14 can therefore be predicted through an interpolation process based on those scattering ray signals. The scattering rays can be reduced by subtracting the interpolated scattering ray signals from the signal values of the region into which the X-rays have entered as detected by the two-dimensional detection unit 14. This process shall be described further with reference to FIG. 6.

Signal G0 in FIG. 6 represents an ideal profile signal occurring when an X-ray beam 13 emitted from a single X-ray source passes through a slit in the slit unit 17, passes through the subject, and is detected by the two-dimensional detection unit 14. This also represents a signal obtained through ideal correction. However, the two-dimensional detection unit 14 actually outputs a signal value such as that represented by G1, due to scattering within the subject. Reducing, to zero, the regions of signal G1 in which the direct components of the X-ray beam 13 enter results in signal G2; signal G2 represents only the scattering rays. Signal G3 indicates the result of predicting scattering rays in the regions in which the direct components of the X-ray beam 13 enter based on signal G2. Note that it is necessary to carry out the prediction calculations having reduced the influence of regions nearby the regions in which the direct components of the X-ray beam 13 enter in signal G2. The range of nearby regions may be determined empirically, or may be determined based on the size of the signal value in the regions in which the direct components enter. Subtracting the predicted scattering signal G3 from signal G1 results in signal G4, which is a signal for which the scattering has been corrected.

Note that a known interpolation technique may be used for the prediction calculations. There are many such known techniques, and resampling, linear (straight line) interpolation, polynomial (spline and so on) interpolation, function fitting, weighted averages, calculus of variations, and so on may be used. For example, the scattering signal prediction can be performed by removing the regions in which the direct components of the X-ray beam 13 enter and carrying out polynomial interpolation, or by reducing the weight of the regions in which the direct components of the X-ray beam 13 enter and using a weighted average.

Returning to FIG. 1, the X-ray beams 13 pass directly through the subject, or are scattered by the subject and then reach the two-dimensional detection unit 14. The two-dimensional detection unit 14 is configured of multiple pixels disposed in grid form. In the present embodiment, each pixel (detector) is configured of a semiconductor detector, but other photoelectric conversion elements may be used. The pixel size of the detector is determined by the size of the lesion to be detected. Mammography for detecting calcifications of several millimeters requires a pixel size of approximately 100 microns, whereas chest imaging for detecting nodules of approximately 1 centimeter requires a pixel size of approximately 200 to 400 microns. The external size of the two-dimensional detection unit 14 is also dependent on the subject of the imaging. Mammography requires an external size of approximately 200 by 240 millimeters, whereas chest imaging requires a size of approximately 430 by 430 millimeters.

A rectangular coordinate system 15 for imaging shall be described next. The X and Y axes represent the directions in which the grids of the multi X-ray generating unit 16 and the two-dimensional detection unit 14 are disposed, while the Z-axis represents the direction in which the X-ray beams 13 are emitted. The X-axis represents the direction in which the movement mechanisms of the multi X-ray generating unit 16 and the slit unit 17 slide those respective units. The mechanism for moving the multi X-ray generating unit 16 is a multi X-ray moving unit 18, whereas the mechanism for moving the slit unit 17 is a slit moving unit 19. In general, when a physician observes an image, s/he observes the image with the body axis of the person following the vertical direction. Because the human eye has a higher resolution in the horizontal direction, it is preferable to increase the resolution in the horizontal direction for diagnostic images as well. Accordingly, when, as shown in FIG. 1, a human body is arranged so that the body axis direction and the X-axis direction match, X-ray beam slices that extend in the Y-axis direction are more advantageous in terms of resolution. In other words, an imaging system in which the X-ray beam slices extending in the Y-axis direction slide along the X-axis direction is desirable.

Figure 4:
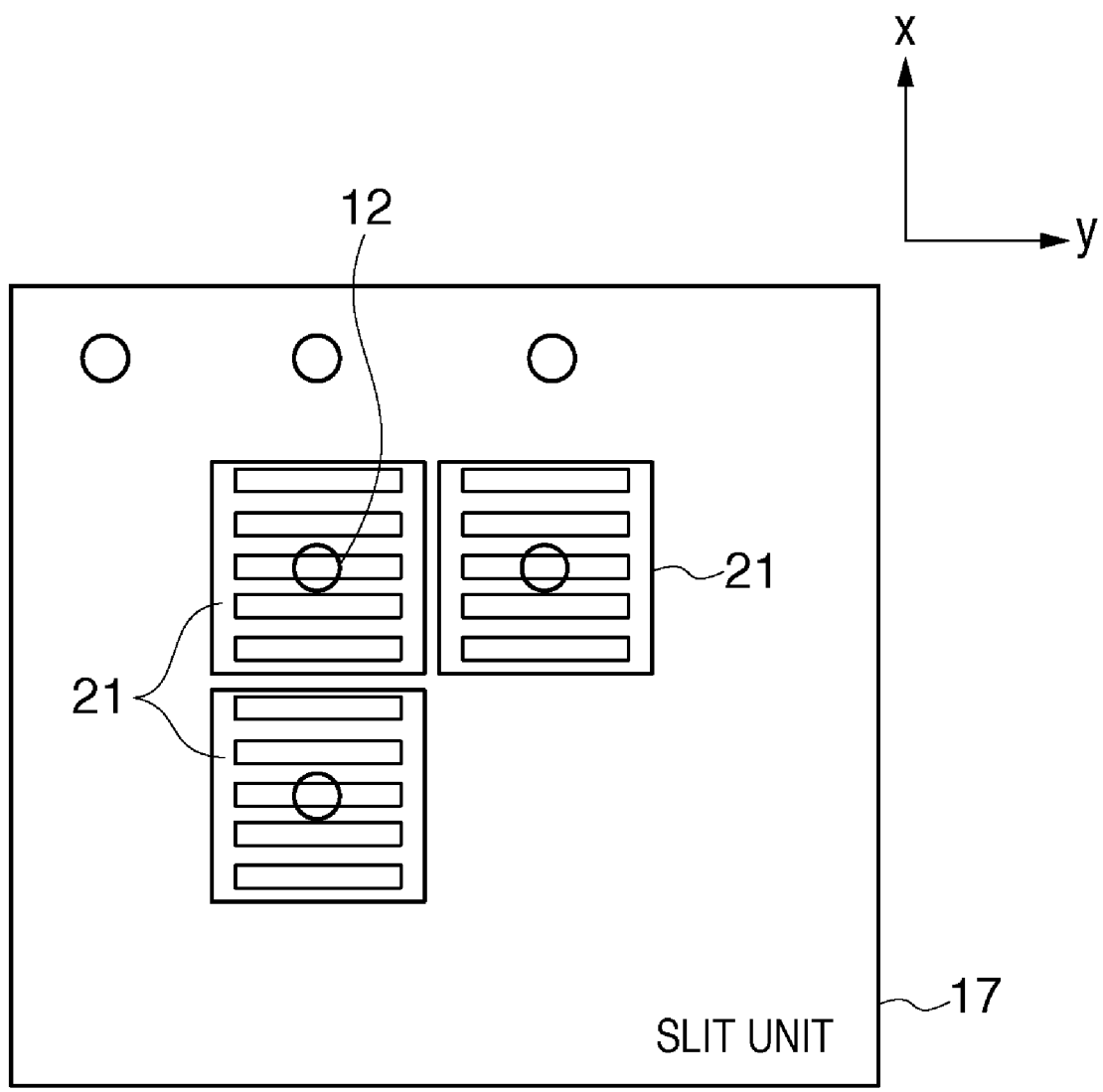
FIG. 4 is a diagram of the XY-plane of the imaging system according to the first embodiment, and illustrates the structure of a slit unit in detail.

FIG. 4 is a diagram viewing the slit unit 17 from the multi X-ray generating unit 16 that is positioned thereabove in the Z-axis direction. Multiple X-ray sources 12 are disposed in grid form in the multi X-ray generating unit 16, and slit boards 21, corresponding to each of the X-ray sources 12, are provided in the slit unit 17. The slit board 21 has a configuration in which multiple slits for shaping the X-ray beams 13 are provided in a lead plate that has high X-ray shielding efficiency. When the X-ray beams 13 are to be formed in slice form, the slits have a rectangular shape extending in the Y direction, as shown in FIG. 4. Although not shown in the drawings, when the X-ray beams 13 are to be small squares in grid form, the slit board 21 has small square slits disposed in grid form.

Figure 2:
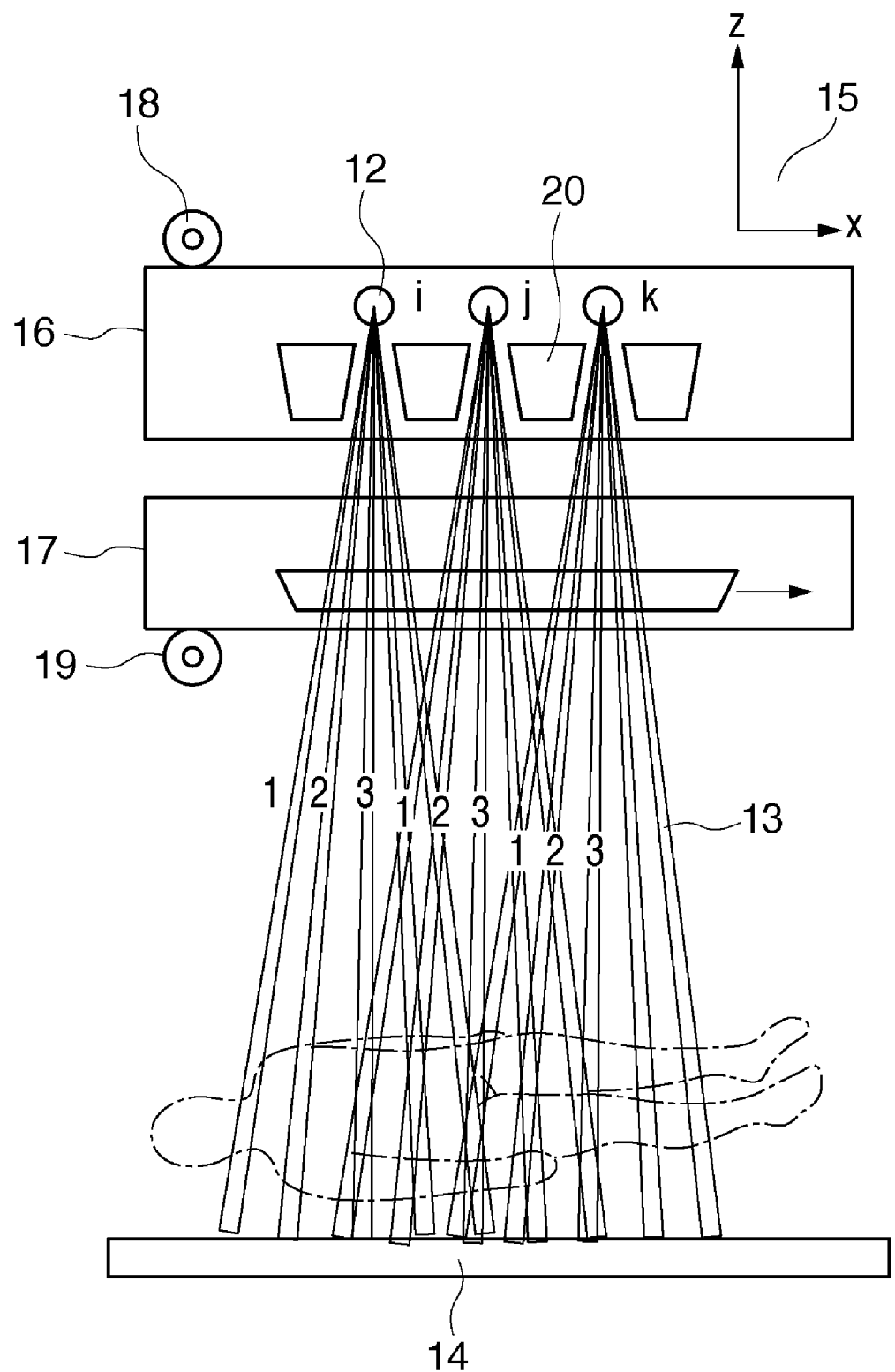
FIG. 2 is a diagram illustrating the XZ-plane of the imaging system according to the first embodiment.

FIG. 2 illustrates the XZ-plane of the imaging system in the case where the slit unit 17 shown in FIG. 4 is used. In FIG. 2, three X-ray sources, or i, j, and k, are illustrated as performing X-ray exposures at the same time; however, in reality, the X-ray sources 12 do not perform exposure at the same time. Rather, the sources are controlled so as to make switched exposures at high speeds. Meanwhile, during the switched exposures, the multi X-ray generating unit 16 and slit unit 17 slide relative to the two-dimensional detection unit 14 while maintaining their positions relative to each other, using the multi X-ray moving unit 18 and the slit moving unit 19. The distance of the slide is the same as the grid pitch p of the multi X-ray generating unit 16. As shall be described later, imaging is performed multiple times during the period in which the multi X-ray generating unit 16 and the slit unit 17 slide an amount equivalent to the grid pitch p, making it possible to collect a proper amount of data among the multiple X-ray sources 12.

Taking the X-ray sources i, j, and k as examples, X-ray beams i1, j1, and k1 are formed as parallel beams, and the interval between each X-ray beam is roughly the same as the grid pitch p. The reason for describing this as "roughly" p is that the multi X-ray generating unit 16 moves for a time Δt, which depends on the exposure interval of the X-ray sources i, j, and k. In other words, assuming that the multi X-ray generating unit 16 moves ΔL during each exposure interval of Δt, the interval between the X-ray beams is ΔL+p. Meanwhile, the interval between the parallel beams can be reduced to approximately half, or p/2, by sliding the multi X-ray generating unit 16 so that the X-ray source i performs exposure from an intermediate point 28 in the path to the X-ray source j (see FIG. 7B). Having the X-ray source i take N number of images at equal intervals while moving to the position of the X-ray source j makes it possible to reduce the interval between parallel beams to p/N. Through this, missing regions in the projection data in an image reconstruction space 27 (that is, data missing regions 31 (see FIG. 7A)) can be eliminated.

Figure 7A:
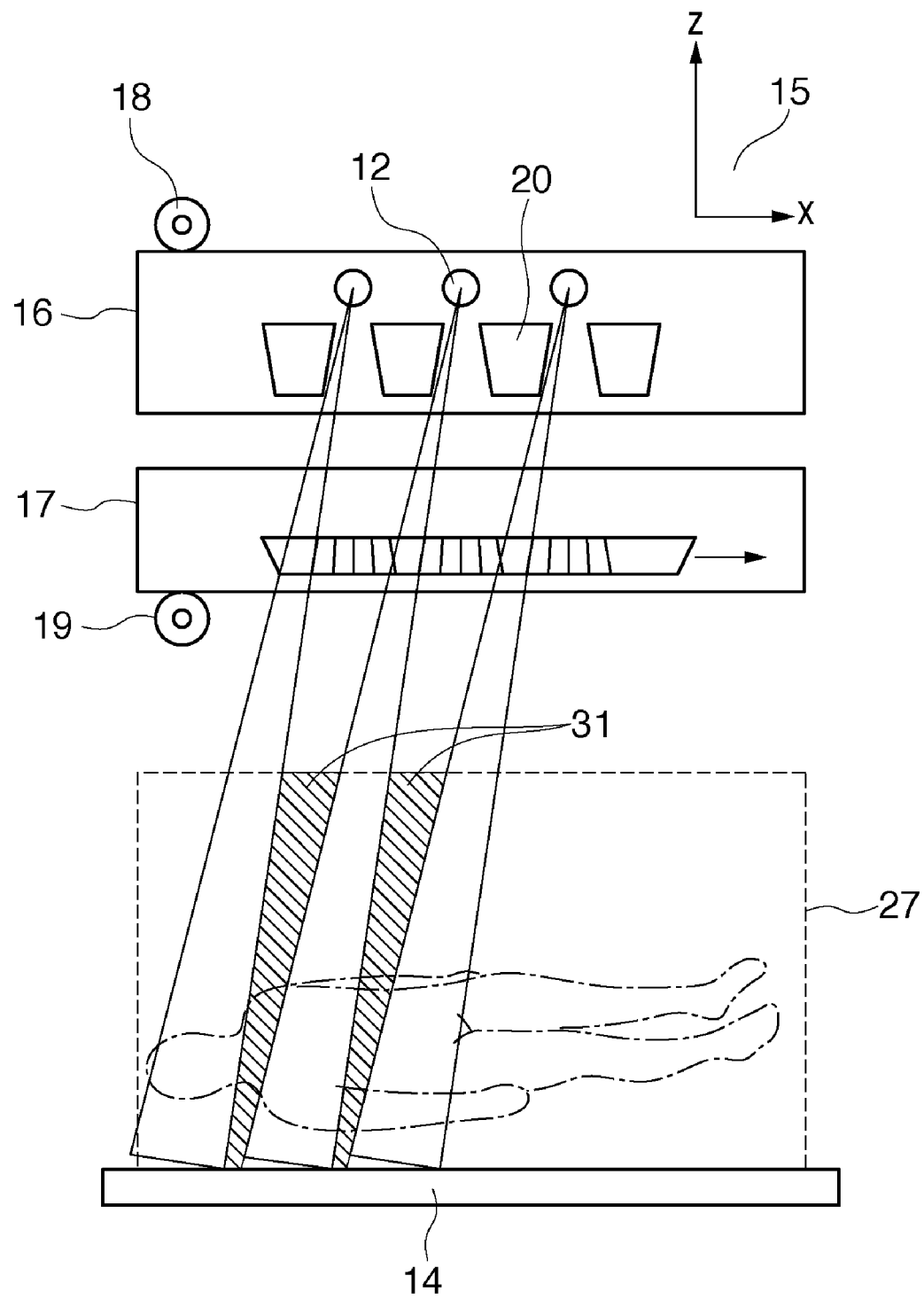
FIG. 7A is a diagram illustrating a relationship between a reconstruction space and data loss according to the first embodiment.

The data missing regions 31 in the image reconstruction space 27 shall be described using FIGS. 7A and B. First, the following assumptions are made:
- the focus size of each X-ray source 12 is 0.5 mm□;
- the grid pitch p of each X-ray source 12 is 15 mm;
- the distance from each X-ray source 12 to the two-dimensional detection unit 14 is 450 mm;
- the distance from each X-ray source 12 to the slit board 21 is 15 mm;
- the width of each slit in each slit board 21 in the X-axis direction is 1 mm; and
- the distance from each X-ray source 12 to the image reconstruction space 27 is 230 mm.

Based on the above, the width of each X-ray beam in the X-axis direction at the position in the image reconstruction space 27 that is closest to the X-ray sources 12 is approximately 8 mm (0.5 mm×an enlargement rate of 15x+0.5 mm). Under these conditions, when data is not collected in the intermediate positions when sliding the multi X-ray generating unit 16, the data in the portions of FIG. 7A indicated by crosshatching (that is, the data missing regions 31) is lost. However, as shown in FIG. 7B, collecting data in the intermediate positions while sliding (the intermediate points 28) eliminates the data missing regions 31.

Figure 7B:
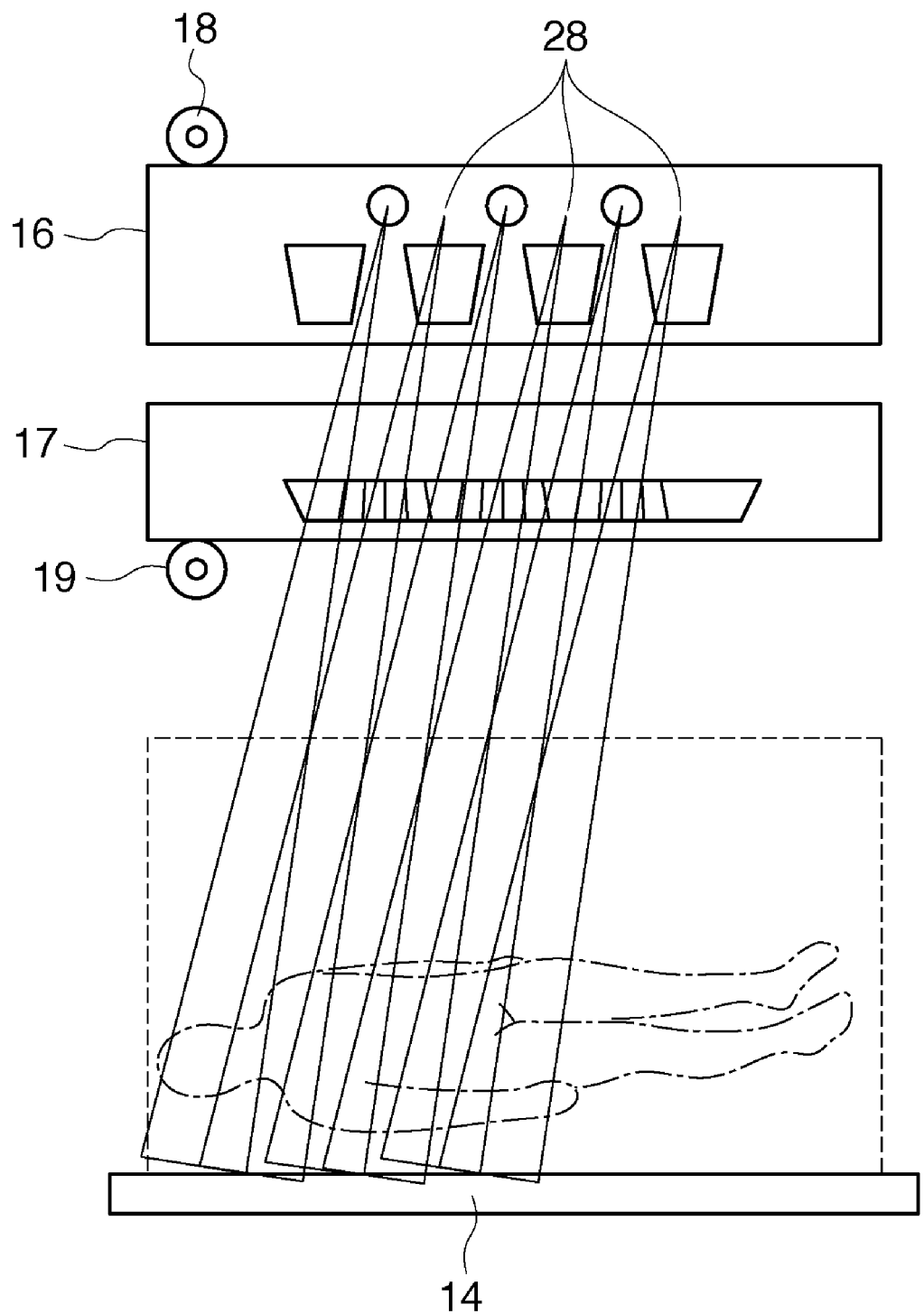
FIG. 7B is a diagram illustrating a relationship between a reconstruction space and data loss according to the first embodiment.

Although exposures are made at the intermediate points 28, which divide the grid pitch p in half, in the examples shown in FIGS. 7A and 7B, the present invention is not limited thereto. X-ray imaging may be executed at multiple positions while moving the multi X-ray generating unit 16 and the slit unit 17 by a predetermined pitch (grid pitch p). Generally, it is possible to make N−1 additional exposures (images) at each part when the grid pitch p has been divided into N equal parts (where N is a natural number of 2 or more). Making N−1 additional exposures in the grid pitch p interval contributes to an improvement in the S/N ratio in the projection data, in addition to preventing the occurrence of the spatial data missing regions 31 shown in FIG. 7A.

Figure 3:
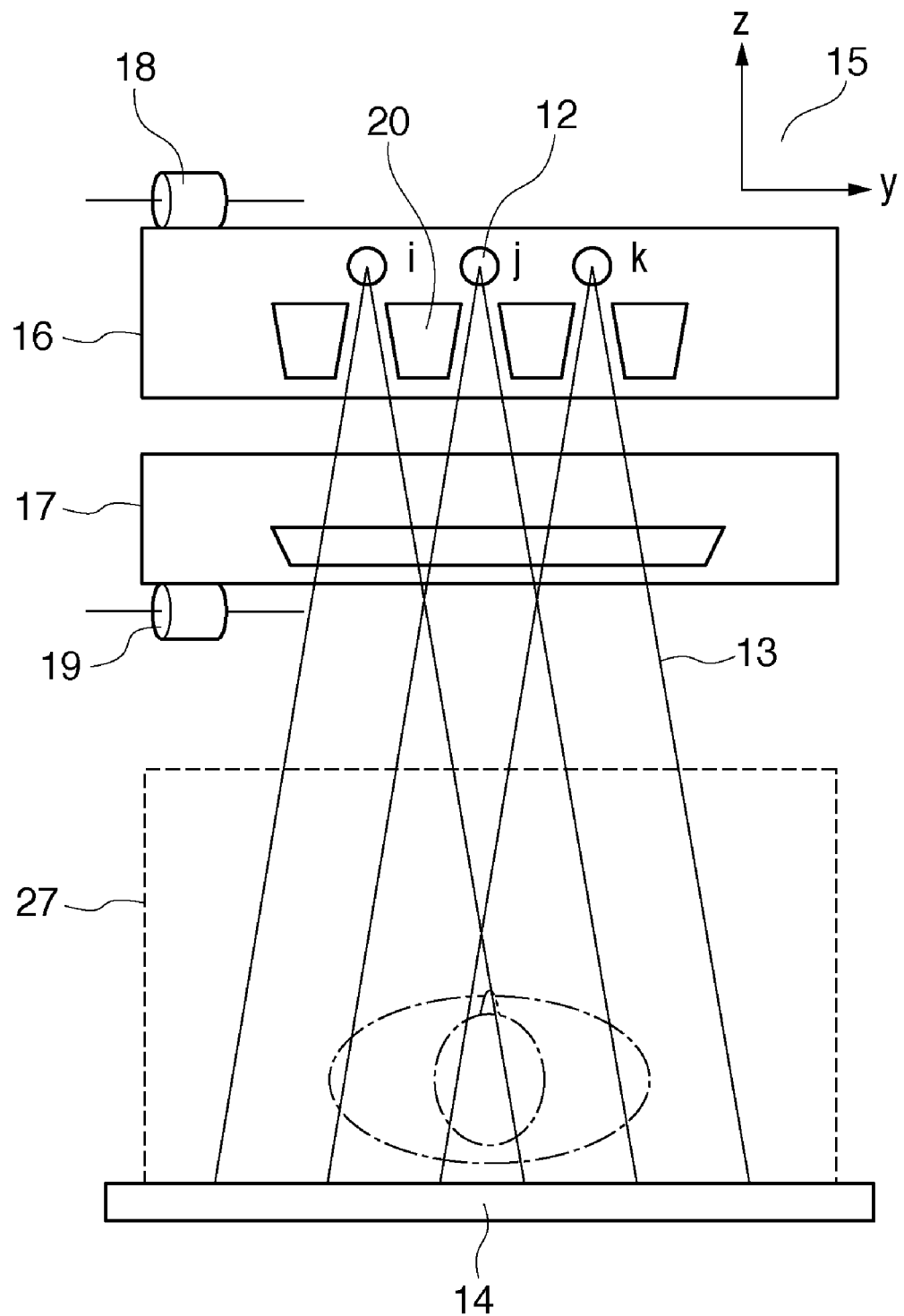
FIG. 3 is a diagram illustrating the YZ-plane of the imaging system according to the first embodiment.
Figure 8:
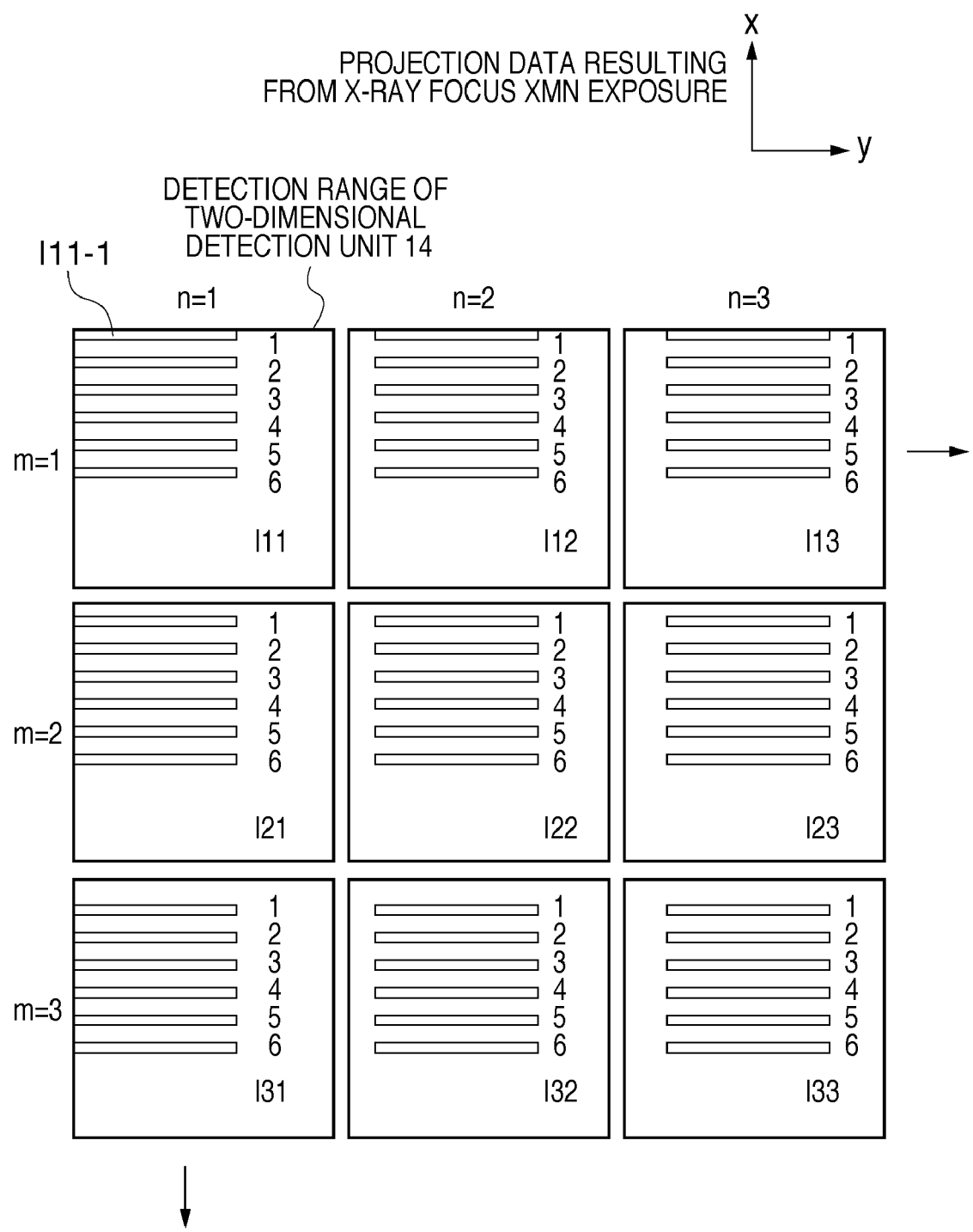
FIG. 8 is a diagram illustrating X-ray images formed upon a two-dimensional detection unit 14 by respective X-ray sources Xmn in the case where switched exposures are made according to the first embodiment.

FIG. 3 illustrates the XY-plane of the imaging system according to the first embodiment. When slice-formed X-ray beams 13 extending in the Y direction are to be formed as shown in FIG. 4, the system is configured so that the entire width of the two-dimensional detection unit 14 in the XY-plane is irradiated by the X-ray beams 13 from each of the X-ray sources 12. Although in FIG. 3, three X-ray sources, or i, j, and k, are illustrated as performing X-ray exposures at the same time, as described earlier, in reality, the multiple X-ray sources 12 do not perform X-ray exposure at the same time. Rather, the sources make switched exposures at high speeds. In the case where the X-ray sources 12 are configured of cold cathodes, high-speed switched exposures with a cycle of approximately 1 msec can be performed with ease. FIG. 8 illustrates X-ray images formed upon the two-dimensional detection unit 14 by each X-ray source Xmn when switched exposure is carried out. In the example shown in FIG. 8, each X-ray source 12 forms six X-ray slices Xmn-h (where h=1 to 6) (not shown) due to the slit unit 17, and X-ray slice images Imn-h (where h=1 to 6) corresponding to each X-ray slice are shown. Note that the X-ray sources Xmn may perform fast-scanning in either the direction in the X-axis or the direction in the Y-axis. In the case where the data from X-ray sources 12 aligned in the X-axis direction (X-ray image data) is to be simultaneously back-projected as parallel data, it is preferable to fast-scan in the X-axis direction, through the procedure shown in FIG. 9A. This is done to image data to be processed simultaneously in a short amount of time.

Figure 5:
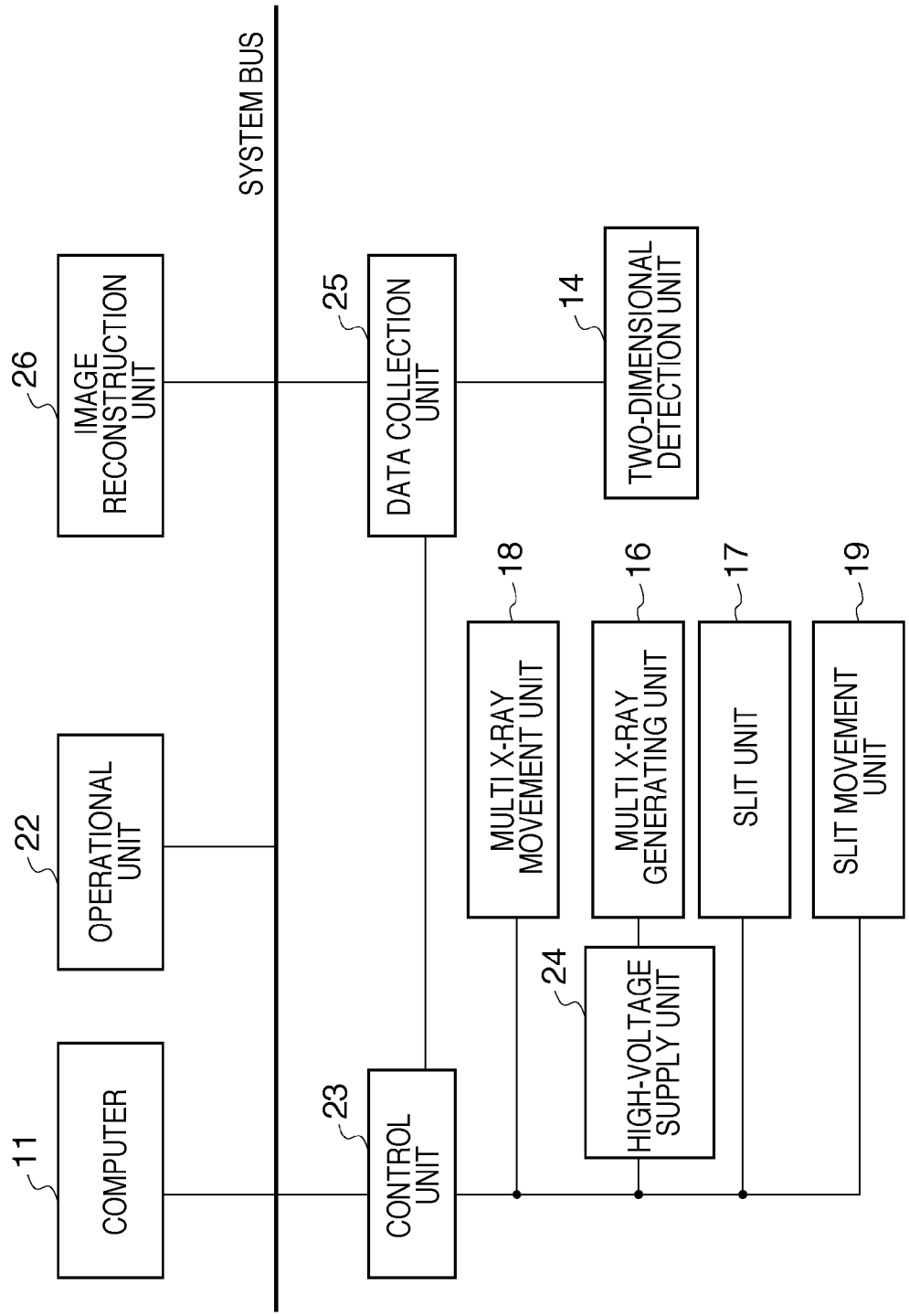
FIG. 5 is a block diagram illustrating an exemplary structure of an imaging system in an X-ray imaging apparatus according to a first embodiment.

FIG. 5 is a block diagram illustrating an example of the configuration of an X-ray imaging system according to the first embodiment. The system of the first embodiment is controlled in its entirety by a computer 11 and a program (not shown). Instructions to start imaging a subject, instructions to reconstruct images, and displaying images are performed via an operational unit 22. When an instruction to start imaging is made through the operational unit 22, a control unit 23 commences control of the various units of which the imaging system is configured.

In other words, the control unit 23 outputs a command to a data collection unit 25, placing the two-dimensional detection unit 14 in a data-collectable state, in accordance with an instruction to start imaging. The control unit 23 then outputs a command to a high-voltage supply unit 24, placing the multiple X-ray sources 12 in a sequential exposure state. The control unit 23 causes the two-dimensional detection unit 14 to collect the X-ray projection data of the subject in synchronization with each exposure. The two-dimensional detection unit 14 digitizes the X-ray projection data and transfers the digitized data to the data collection unit 25. The control unit 23 then controls the multi X-ray moving unit 18 and the slit moving unit 19 in parallel with the stated multiple exposure data collections, and slides the multi X-ray generating unit 16 and the slit unit 17 while maintaining their relative positional relationship.

Figure 9B:
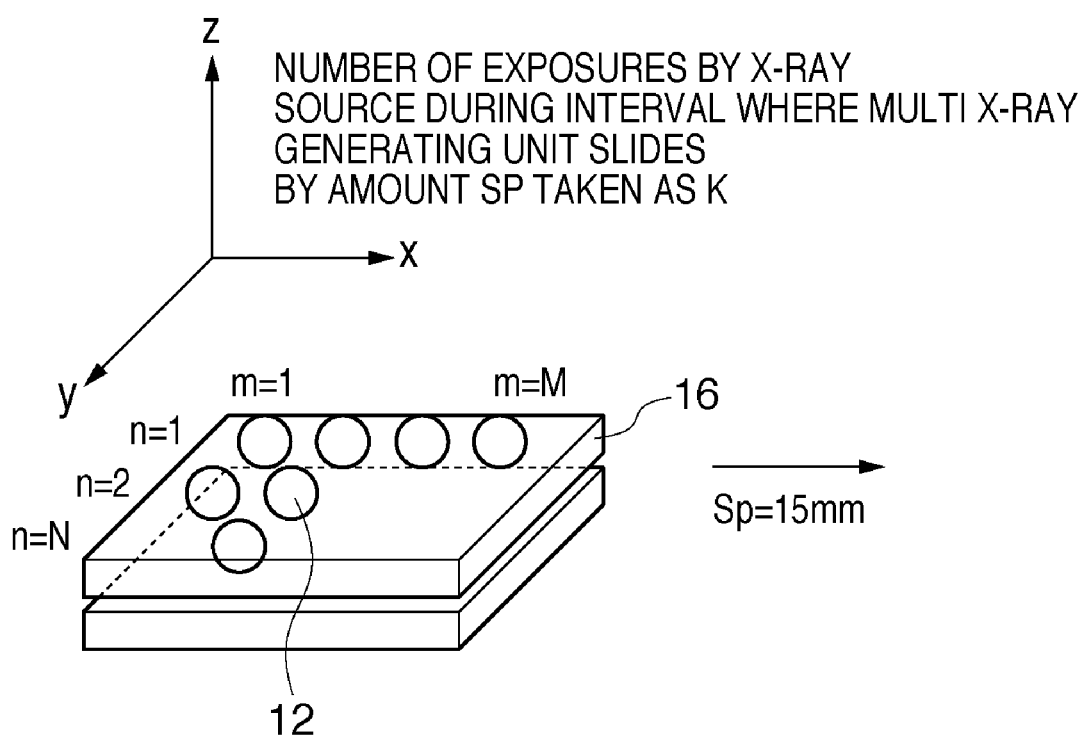
FIG. 9B is a diagram illustrating an example of a two-dimensional array of X-ray sources according to the first embodiment.

FIG. 9A is a flowchart illustrating a data collection process performed by the data collection unit 25. In the procedure of FIG. 9A, fast-scanning is performed in the X-axis direction. Here, as shown in FIG. 9B, M represents the number of X-ray sources 12 disposed in the X-axis direction, N represents the number of X-ray sources 12 disposed in the Y-axis direction, and K represents the number of exposures by each X-ray source (Xmn) during the period in which the multi X-ray generating unit 16 slides by an amount Sp. In step S100, the data collection unit 25 resets the variables k, m, and n to 1. Then, in step S101, the data collection unit 25 commences data collection through X-ray exposure performed by the X-ray sources Xmn, and also starts sliding the multi X-ray generating unit 16 and the slit unit 17. In the first embodiment, the slit unit 17 and the multi X-ray generating unit 16 slide with their relative positions being held the same. In step S102, an image Imnk resulting from an exposure Xmnk is stored in the data collection unit 25. Here, k represents the number of exposures by each X-ray source Xmn during the period in which the multi X-ray generating unit 16 slides by the amount Sp. In steps S103 and S104, the X-ray images resulting from sequentially driving M X-ray sources aligned in the X-axis direction are collected first. When this imaging has been performed by M X-ray sources, in steps S105 and S106, m is reset to 1, and the X-ray images resulting from sequentially driving M X-ray sources aligned in the X-axis direction are then collected in the next row (that is, the adjacent row in the Y direction (n=n+1)). This process is repeated until the Nth row. When the process has ended for the Nth row, the variables m and n are reset to 1, k is incremented by 1, and the process returns to step S101. This process is repeated K number of times during the slide interval (steps S107 and S108).

Next, when image reconstruction has been instructed through the operational unit 22, the projection data stored in the data collection unit 25 is sequentially transferred to an image reconstruction unit 26, and three-dimensional volume data is reconstructed. Although filter correction back-projection is appropriate for the image reconstruction, successive approximation may be used for the image reconstruction as well. A characteristic of the present embodiment is that the projection data makes up the parallel data. As shown in FIG. 2, the X-ray beams i1, j1, and k1 and the X-ray beams i2, j2, and k2 each create respective parallel beams. Similarly, as shown in FIG. 7B, data from the same exposure direction collected while the multi X-ray generating unit 16 and the slit unit 17 slide (Sp/2, Sp/3, and so on) also creates beams parallel to the X-ray beams i1, j1, and k1 and the X-ray beams i2, j2, and k2. Although the projection data is stored in the data collection unit 25 at each exposure, this data is transferred to the image reconstruction unit 26 after a process for constructing that data as parallel data (that is, sorting) has been performed.

Next, a data cut-out process and a data sorting process for constructing parallel data shall be described. As indicated by signal G0 in FIG. 6, the transmitted X-ray data is formed locally upon the two-dimensional detection unit 14. The data cut-out process is performed after the scattering ray correction shown in FIG. 6. Performing the scattering ray correction prior to the data cut-out process and the data sorting process makes it possible to reduce the amount of memory required for processing and reduce the number of memory accesses.

The data cut-out process is a process for geometrically cutting out a region that has been irradiated by X-rays from the overall image on the two-dimensional detection unit 14, such as that exemplified by X11-1 in FIG. 8. The position of the portion Xmn-h that has been irradiated by X-rays within the overall image on the two-dimensional detection unit 14 can be calculated based on the X-ray exposure timing. However, the reconstruction of the parallel data is not limited to putting the X-ray slice images Imn-h corresponding to the X-ray slices Xmn-h in sequence. For example, L number of X-ray slice images can be constructed by slicing the X-ray slice image Imn-h in the X-axis direction and putting the resulting slices in sequence. Increasing the number of divisions makes it possible to increase how parallel the parallel data is. For example, strictly speaking, the image Imn-h is fan data, and is thus not strictly parallel data even if spliced together. Breaking the data down to two-dimensional detector element rows makes it possible to obtain more complete parallel data.

As described thus far, the set of X-ray slice images I11-1, I21-1, and I31-1, the set of X-ray slice images I11-2, I21-2, and I31-2, and the set of X-ray slice images I12-1, I22-1, and I32-1 shown in FIG. 8 each make up parallel data. The data sorting process is a process that focuses upon that fact, splicing together sets on a set-by-set basis (a unit-by-unit basis for parallel data) into a single image.

Figure 10:
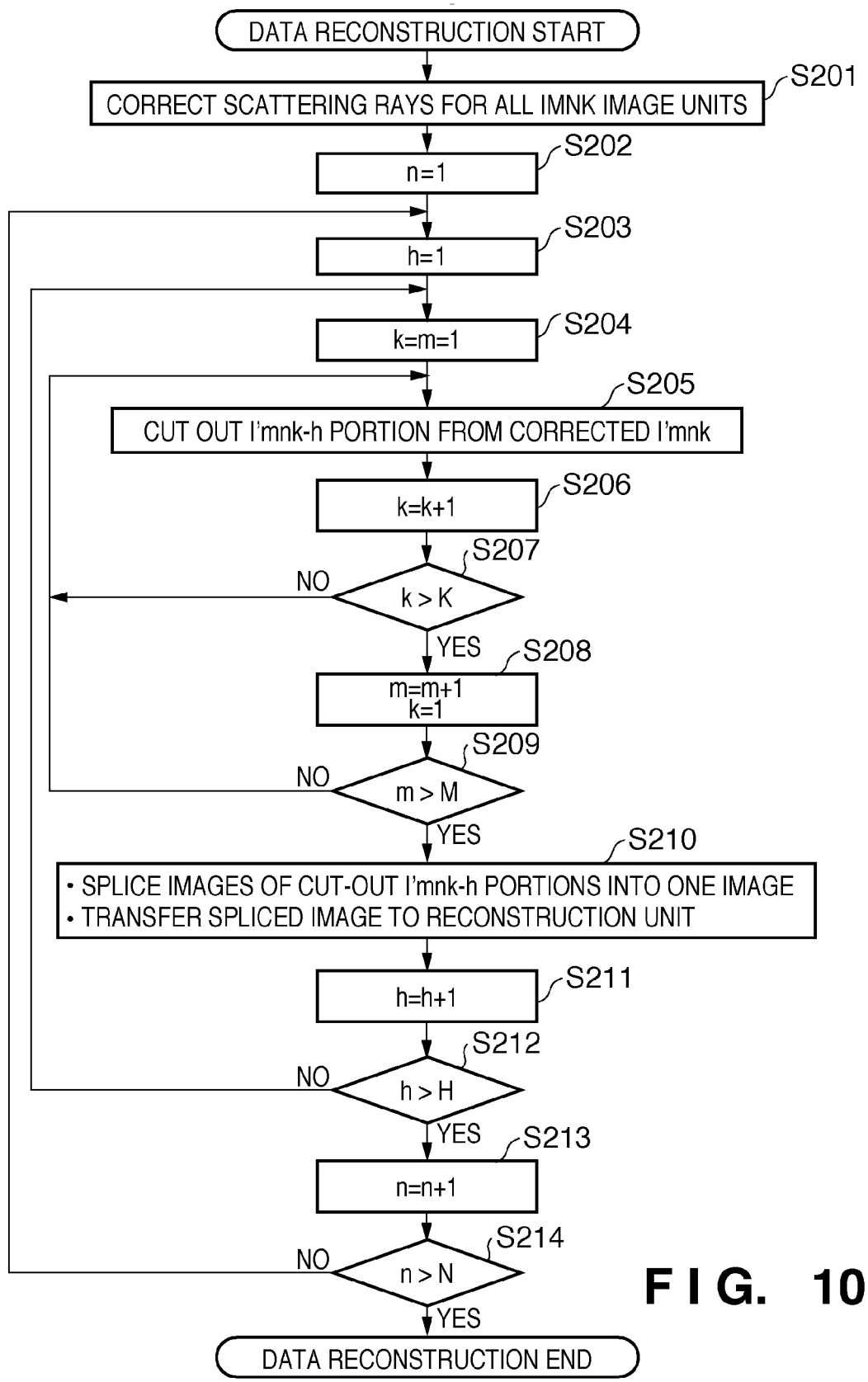
FIG. 10 is a flowchart illustrating a data reconstruction process according to the first embodiment.

FIG. 10 is a flowchart illustrating the data reconstruction process described above. Here, as shown in FIG. 9B, M represents the number of X-ray sources 12 disposed in the X-axis direction, N represents the number of X-ray sources 12 disposed in the Y-axis direction, and K represents the number of exposures by each X-ray source Xmn during the period in which the multi X-ray generating unit 16 slides by an amount Sp. In step S201, the image reconstruction unit 26 executes the scattering ray correction described in FIG. 6 taking the image Imnk stored in the data collection unit 25 as the processing unit (in FIG. 8, for example, the X-ray slice images I11-1 to I11-6 are taken as the processing unit). In steps S202 to S204, the variables n, h, k, and m are set to their initial values. Next, in step S205, the region corresponding to the hth slit is cut out from a corrected image I'mnk, obtained by performing the scattering ray correction on the image Imnk, and is taken as I'mnk-h. This process is repeated for a slit and each X-ray source at all slide positions (k=1 to K) (steps S206 and S207). Then, if the process has ended for an X-ray source, the above processing is repeated for the X-ray source adjacent in the X direction (S208 and S209). In this manner, from steps S205 to S209, the X-ray image from the same hth slit is cut out for each X-ray source 12 aligned in the X direction (that is, the X-ray image obtained from a slice beam formed by slits whose relative positional relationship with the X-ray source match). Then, in step S210, a single image is then spliced together, focusing on the fact that the cut-out images I'mnk-h make up parallel data. The image that has been spliced together is transferred to the image reconstruction unit 26, after which filter correction back projection processing is carried out.

The image reconstruction unit 26 performs the above process for each slit (in the example shown in FIG. 8, each slit where h=1 to 6) (steps S211 and S212). Furthermore, when the above process has been performed on all slits for the same n value, the next row (the row adjacent in the y direction) is to be processed; therefore, n is incremented by 1, and the process returns to step S203 (steps S213 and S214). Note that for each set, for example, separate back-projection may be carried out as parallel data whose incoming X-ray directions are different. Here, the number of slit positions H is not limited to the actual number of slits, and may be an integral multiple of the actual slit number. Increasing the number of slit positions H can improve how parallel the spliced image is. Repeating the above processing until n>N results in the data being reconstructed.

The image reconstruction unit 26 then back-projects the image transferred from the data collection unit 25 into an internal 3D memory space. The back-projection algorithm can employ a known technique. With filter correction back projection processing, a filtering process that removes the direct components of the image transferred from the data collection unit 25 is first performed, after which the data is back-projected based on a geometric system obtained through data collection. In the preceding descriptions, a reconstruction method that performs back-projection after the data has been sorted as parallel data has been discussed, but the reconstruction method is not limited thereto, and direct reconstruction, where the fan data is reconstructed as-is, may be used as well.

As described thus far, according to the first embodiment, it is possible to collect projection data of high density with respect to a 3D space that makes up a subject region. X-ray beams are simultaneously constructed in slit form, making it possible to improve the accuracy of scattering ray correction through image processing. Furthermore, enabling scattering ray correction through image processing eliminates the need for a scattering ray correction grid, making it possible to reduce the amount of radiation the subject (a patient) is exposed to.

Second Embodiment

Figure 11:
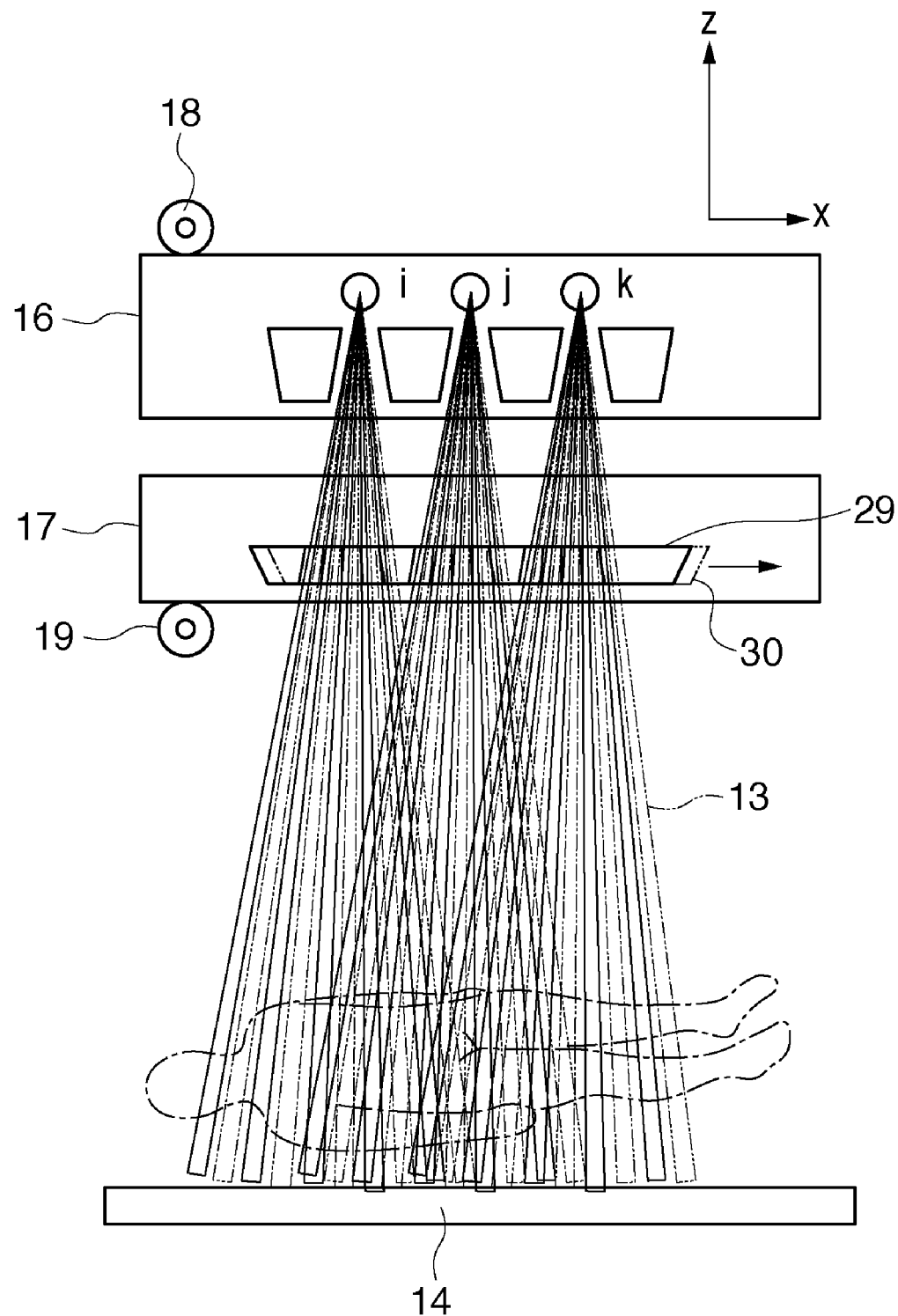
FIG. 11 is a diagram illustrating the XZ-plane of the imaging system according to a second embodiment.

FIG. 11 is a diagram illustrating an example of the configuration of an X-ray imaging system according to a second embodiment. Hereinafter, the differences between the present embodiment and the first embodiment shall be described. In the first embodiment, the multi X-ray generating unit 16 and the slit unit 17 slide with their relative positional relationships matching. However, in the second embodiment, the multi X-ray generating unit 16 and the slit unit 17 slide so that their relative positional relationships change. The purpose of moving these units so their relative positions change is to increase the number of directions for the X-ray beam slices that irradiate the subject, thereby improving the image quality of the reconstructed image. FIG. 11 illustrates the X-ray beams 13 that pass through the slits when the slit unit 17 is at (1) a position 29 and at (2) a position 30, assuming that the position of the multi X-ray generating unit 16 is fixed. It can be seen that X-ray beams 13 that irradiate the subject from different directions in the 3D space that makes up the subject are emitted. In the second embodiment, too, the multi X-ray generating unit 16 moves by an amount equivalent to the grid pitch p relative to the two-dimensional detection unit 14, until the imaging stops. The slit unit 17 makes a round-trip pass relative to the multi X-ray generating unit 16. When X-ray data is obtained during this round-trip pass, it is possible to image parallel projection data in different directions. Thus, like the first embodiment, it is possible to collect and reconstruct image data for each instance of parallel projection data.

Although in FIG. 11, X-ray exposure is carried out only in the two relative positions, or (1) and (2), it should be noted that there are multiple situations in which the multi X-ray generating unit 16 and the slit unit 17 have a different relative positional relationship. In other words, X-ray exposure can be performed in three or more relative positional relationships as well. Note that the movement is equivalent to the pitch interval in the X direction of the slits. Furthermore, because it is difficult to ensure that the relative positions of the multi X-ray generating unit 16 and the slit unit 17 are the same for each X-ray source 12, the direct method for back-projecting each projection image as-is is used as the reconstruction algorithm. Finally, the variation of the relative positions is not limited to the direction in which the multi X-ray generating unit 16 slides, the projection data from different irradiation angles can be collected even if the variation occurs in the direction perpendicular to the slide direction.

As described thus far, according to the second embodiment, it is possible to improve the number of the various irradiation angles with respect to a 3D space that makes up a subject region, making it possible to improve the resolution of the reconstructed image and the S/N ratio.

Embodiments of the present invention have been described in detail above, but the present invention can take the form of a system, apparatus, method, program, storage medium, and so on. Specifically, the present invention may be applied to a system configured of multiple devices or to an apparatus configured of a single device.

Note that the case where the functionality of the above-mentioned embodiments is achieved by directly or remotely supplying a software program to a system or device and reading out and executing the supplied program code through a computer in the system or device is included in the scope of the present invention. In this case, the supplied program is a computer program that corresponds to the flowchart indicated in the drawings in the embodiments.

Accordingly, the program code itself, installed in a computer so as to realize the functional processing of the present invention through a computer, also realizes the present invention. In other words, the computer program itself, for realizing the functional processing of the present invention, is also included within the scope of the present invention.

In this case, a program executed through an interpreter or object code, script data supplied to an OS, or the like may be used, as long as it has the functions of the program.

Examples of the a computer readable storage medium that can be used to supply the computer program include Floppy® disks, hard disks, optical disks, magneto-optical disks, MOs, CD-ROMs, CD-Rs, CD-RWs, magnetic tape, non-volatile memory cards, ROMs, and DVDs (DVD-ROMs, DVD-Rs).

Using a browser of a client computer to connect to an Internet homepage and downloading the computer program of the present invention to a storage medium such as a hard disk can be given as another method for supplying the program. In this case, the downloaded program may be a compressed file including a function for automatic installation. Furthermore, this method may be realized by dividing the program code that makes up the program of the present invention into multiple files and downloading each file from different homepages. In other words, a WWW server that allows multiple users to download the program files for realizing the functional processing of the present invention through a computer also falls within the scope of the present invention.

Furthermore, the program of the present invention may be encrypted, stored in a storage medium such as a CD-ROM, and distributed to users. In this case, a user that has cleared a predetermined condition is allowed to download key information for removing the cryptography from a homepage via the Internet, use the key information to decrypt the program, and install the program on a computer.

Also, the functions of the embodiments may be realized, in addition to through the execution of a loaded program using a computer, through cooperation with an OS or the like running on the computer based on instructions of the program. In this case, the OS or the like performs part or all of the actual processing, and the functions of the above-described embodiments are realized by that processing.

Furthermore, the functions of the aforementioned embodiments may be partially or completely implemented by writing the program that has been read out from the storage medium into the memory of a function expansion board installed in a computer or a function expansion unit connected to a computer. In this case, after the program has been written into the function expansion board or the function expansion unit, a CPU or the like included in the function expansion board or the function expansion unit performs part or all of the actual processing based on the instructions of the program.

According to the present invention, in X-ray imaging that uses a multi X-ray source, data missing regions arising in pitch intervals between X-ray sources can be reduced or eliminated, and the influence of scattering rays can be reduced.

While the present invention has been described with reference to an exemplary embodiment, it is to be understood that the invention is not limited to the disclosed exemplary embodiment. The scope of the following claims is to be accorded the broadest interpretation so as to encompass all such modifications and equivalent structures and functions.

This application claims the benefit of Japanese Patent Application No. 2008-068355, filed Mar. 17, 2008, which is hereby incorporated by reference herein in its entirety.

What is claimed is:

1. An X-ray imaging apparatus comprising:
a multi X-ray generating unit in which multiple X-ray foci are disposed in two-dimensional form at a predetermined pitch in a first direction;
a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction;
a two-dimensional detection unit that detects the X-ray intensity of the X-ray beams formed by the slit unit at a detection surface;
a moving unit that moves the multi X-ray generating unit and the slit unit in the first direction while keeping the relative positional relationship therebetween;
an executing unit that executes X-ray imaging at multiple positions while the moving unit moves the multi X-ray generating unit and the slit unit by the amount of the predetermined pitch; and
a reconstructing unit that reconstructs an X-ray image based on the X-ray intensity obtained through the X-ray imaging executed by the executing unit.

2. The apparatus according to claim 1,
wherein the reconstructing unit includes a sorting unit that sorts X-ray image data for each instance of parallel data, the parallel data being X-ray image data obtained from X-ray beams formed by slits in the multiple slit members whose relative positional relationship with the X-ray source is the same; and
a three-dimensional image is reconstructed based on the X-ray image data sorted by the sorting unit.

3. The apparatus according to claim 1, further comprising a correcting unit that removes the influence of scattering rays from X-ray image data obtained by the two-dimensional detection unit detecting an X-ray beam emitted from one X-ray focus and formed by the slit member opposite thereto,
wherein the reconstructing unit uses the X-ray image data corrected by the correcting unit.

4. An X-ray imaging apparatus comprising:
a multi X-ray generating unit in which multiple X-ray foci are disposed in two-dimensional form at a predetermined pitch in a first direction;
a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction;
a two-dimensional detection unit that detects the X-ray intensity of the X-ray beams formed by the slit unit at a detection surface;
a moving unit that moves the multi X-ray generating unit and the slit unit in the first direction while changing the relative positional relationship therebetween;
an executing unit that executes X-ray imaging at multiple positions while the moving unit moves the multi X-ray generating unit and the slit unit by the amount of the predetermined pitch; and
a reconstructing unit that reconstructs an X-ray image based on the X-ray intensity obtained through the X-ray imaging executed by the executing unit.

5. A control method for an X-ray imaging apparatus, the apparatus including:
a multi X-ray generating unit in which multiple X-ray foci are disposed in two-dimensional form at a predetermined pitch in a first direction;
a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction; and
a two-dimensional detection unit that detects the X-ray intensity of the X-ray beams formed by the slit unit at a detection surface,
the method comprising the steps of:
moving the multi X-ray generating unit and the slit unit in the first direction while keeping the relative positional relationship therebetween;
executing X-ray imaging at multiple positions while the step of moving moves the multi X-ray generating unit and the slit unit by the amount of the predetermined pitch; and
reconstructing an X-ray image based on the X-ray intensity obtained through the X-ray imaging executed in the step of executing.

6. A non-transitory computer-readable storage medium on which is stored a program for causing a computer to execute the control method according to claim 5.

7. A control method for an X-ray imaging apparatus, the apparatus including:
a multi X-ray generating unit in which multiple X-ray foci are disposed in two-dimensional form at a predetermined pitch in a first direction;
a slit unit having multiple slit members each disposed opposite to its respective X-ray focus, and each slit member having multiple slits arranged in the first direction, each of the slits forming an X-ray from the X-ray focus opposite thereto into a slice-formed X-ray beam whose lengthwise direction is a second direction that is different from the first direction; and
a two-dimensional detection unit that detects the X-ray intensity of the X-ray beams formed by the slit unit at a detection surface,
the method comprising the steps of:
moving the multi X-ray generating unit and the slit unit in the first direction while changing the relative positional relationship therebetween;
executing X-ray imaging at multiple positions while the step of moving moves the multi X-ray generating unit and the slit unit by the amount of the predetermined pitch; and
reconstructing an X-ray image based on the X-ray intensity obtained through the X-ray imaging executed in the step of executing.

8. A non-transitory computer-readable storage medium on which is stored a program for causing a computer to execute the control method according to claim 7.

* * * * *